United States Patent
Dera et al.

(10) Patent No.: US 8,722,962 B2
(45) Date of Patent: May 13, 2014

(54) WOUND DRESSING APPLICATOR

(75) Inventors: Ian Dera, London (GB); Dimitrios Scoutas, Melbourne (AU); Matthew Hannant, London (GB); Graeme Maisey, Surrey (GB); Phillip Michael Dunn, Hampshire (GB); Barry Sandbank, Chester (GB); Sushma Rani Jassal, Dublin (IE)

(73) Assignee: Smith & Nephew, Inc., Memphis, TN (US)

(*) Notice: Subject to any disclaimer, the term of this patent is extended or adjusted under 35 U.S.C. 154(b) by 582 days.

(21) Appl. No.: 12/809,518

(22) PCT Filed: Dec. 12, 2008

(86) PCT No.: PCT/GB2008/004115
§ 371 (c)(1), (2), (4) Date: Jan. 21, 2011

(87) PCT Pub. No.: WO2009/081096
PCT Pub. Date: Jul. 2, 2009

(65) Prior Publication Data
US 2011/0118645 A1 May 19, 2011

(30) Foreign Application Priority Data
Dec. 21, 2007 (GB) .................................. 0725087.1

(51) Int. Cl.
*A61F 13/00* (2006.01)
(52) U.S. Cl.
USPC ............................................... 602/48; 221/74
(58) Field of Classification Search
USPC .............. 602/41–54; 221/24–25, 72–74, 185, 221/251; 222/80
See application file for complete search history.

(56) References Cited

U.S. PATENT DOCUMENTS

| 1,646,365 | A |   | 10/1927 | Willis ........................... 604/289 |
| 2,145,779 | A | * | 1/1939  | Puderbaugh .................... 222/80 |
| 4,900,303 | A | * | 2/1990  | Lemelson ..................... 604/514 |
| 4,915,227 | A |   | 4/1990  | Johns ........................... 206/441 |

(Continued)

FOREIGN PATENT DOCUMENTS

| DE | 2947275       | 6/1980 |
| WO | WO 83/02586   | 8/1983 |
| WO | WO 2005/079822 | 9/2005 |

OTHER PUBLICATIONS

Office Communication, issued in Great Britain application No. GB0725087.1, dated Mar. 19, 2008.

(Continued)

*Primary Examiner* — Michael A. Brown
(74) *Attorney, Agent, or Firm* — Fulbright & Jaworski LLP

(57) ABSTRACT

A wound dressing applicator (10) for applying hydrocolloid dressings, compositions for tissue regeneration and the like to a patient's skin. Known wound dressing applicators do not effectively protect against contamination of the wound dressing and/or can be fiddly and difficult to operate and be rendered unusable by unwanted premature separation of the various layers of material adhered to one another. The present applicator comprises a rigid body (20) having a rigid body enclosure (30) for receiving a wound dressing, and an ejector (40) for ejecting the wound dressing from the rigid body enclosure and onto a patient's wound. This enables effective and aseptic handling of a wound dressing and application of the wound dressing onto a patient's wound.

18 Claims, 4 Drawing Sheets

(56) References Cited

U.S. PATENT DOCUMENTS

| | | | | |
|---|---|---|---|---|
| 5,996,931 | A * | 12/1999 | Neveu et al. | 242/597.5 |
| 6,299,018 | B1 * | 10/2001 | Kimbrell | 221/71 |
| 6,676,908 | B2 * | 1/2004 | Robinson et al. | 422/265 |
| 2003/0071051 | A1 * | 4/2003 | Martinsen | 221/70 |
| 2003/0072750 | A1 * | 4/2003 | Rosenberg | 424/94.63 |
| 2003/0136274 | A1 | 7/2003 | Caskey et al. | 99/494 |
| 2005/0127084 | A1 | 6/2005 | McDaniel et al. | 221/33 |
| 2006/0097002 | A1 * | 5/2006 | Chavez | 221/251 |
| 2006/0282034 | A1 | 12/2006 | Faasse | 602/57 |

OTHER PUBLICATIONS

PCT International Preliminary Report on Patentability, issued in International application No. PCT/GB2008/004115, mailed Jun. 22, 2010.

* cited by examiner

WOUND DRESSING APPLICATOR

CROSS-REFERENCE TO RELATED APPLICATIONS

The present application is a national phase application under 35 U.S.C. §371 of International Patent Application PCT Application No. PCT/GB2008/004115, filed 12 Dec. 2008, which claims priority to Great Britain Application No. 0725087.1, filed 21 Dec. 2007. The entire contents of these applications are incorporated herein by reference.

The invention provides a wound dressing applicator. Preferred embodiments of the invention provide a wound dressing applicator comprising a rigid body having an enclosure for wound dressings such as hydrocolloid dressings and compositions for tissue regeneration.

One type of known wound dressing delivery system comprises flexible means for applying the wound dressing to an area of skin. For example, U.S. Pat. No. 4,915,227 provides a dressing delivery system wherein the opening of the packaging and the application of the dressing is accomplished in one fluid motion. Flexible packaging sheets are peeled apart to expose an adhesive coated dressing which is applied to the wound area, whereby the flexible packaging is removed and discarded.

A problem associated with this type of known wound dressing application system is that the means for applying the wound dressing to the patient's skin is flexible, which means that it can be difficult to handle the dressing and to accurately position it to cover a wound. Also, the use of flexible packaging sheets does not adequately protect the wound dressing from damage during transit and general handling of the wound dressing delivery systems.

A further problem with this known type of wound dressing delivery system is that it is reliant on the effectiveness of the adhesives used to seal the outer packaging and to adhere the packaging to the dressing so that the packaging can be used to position the dressing to cover a wound on the patient's skin. If the adhesive properties are incorrectly controlled, the packaging may peel apart prematurely, which could result in contamination of the bandage, or an inability to apply correctly the wound dressing to the skin by using the packaging to handle it, rendering the wound dressing delivery system unusable.

Furthermore, peeling the layers of packaging apart to expose the bandage can be a fiddly task, especially in environments where the user is required to wear protective gloves, such as in a hospital or doctor's surgery.

A further type of known wound dressing delivery system provides rigid handle portions which are used to support an adhesive wound dressing when it is applied to an area of skin, whereupon the handle portions are removed and discarded. An example of this arrangement is provided in US patent publication no. US 2006/0282034 which provides a medical adhesive dressing in which a release liner is peeled back to expose an adhesive dressing supported at rigid handle members which are used to position the wound dressing over a wound, before the handle members are removed and discarded.

A problem associated with this type of known wound dressing application system is that effective operation of the application system is reliant on the effectiveness of the adhesives used to hold the various layers together. If the adhesion between layers is outside of certain tolerances, then the various layers of the application system could not be peeled apart in the required order. The system would not therefore function as it is intended, meaning that the bandage could not be correctly applied to the wound and therefore rendering the wound dressing application system unusable.

A further problem is that as parts of these wound dressing application systems (e.g. backing layers) have to be peeled away to expose the adhesive surface of the wound dressing, the wound dressing application system must be handled by the user to support it while the backing layers are removed. This manual handling has the potential for contaminating or damaging the wound dressing, which would render the application system unusable. It may also be fiddly to remove the backing layers, especially where the user is wearing surgical gloves or the like.

Furthermore, although rigid handle portions are provided to support the wound dressing while it is applied to skin, when the wound dressing itself is flexible, handling the system to accurately position the dressing onto the skin can be difficult.

A problem that is common to both of the aforementioned types of wound dressing application system is that both of the user's hands are required to position and apply the dressing to a patient's wound. This means that the user does not have a free hand available to provide stability when attempting to reach the location of the wound, or to perform other tasks.

DE-A-2947275 discloses a wound dressing container for sterile storage and application. The bandage is stored in a semi-cylindrical cap, made of polystyrene, polypropylene or polyethylene, with the open end closed by a flat foil which is permeable to gas but is fluid tight. The semi-cylindrical cap has two parallel notches which hold down the tops of the sticking plaster whilst the space between them accommodates the pad. To apply the dressing the flat foil is torn off and the pad with the sticking plaster is pressed by the cap against the skin of the patient.

A disadvantage of the bandage and container arrangement of DE-A-2947275 is that the bandage needs an adhesive layer to hold it in place in the container once the flat foil is torn off to avoid the bandage dropping out. This makes for a fiddly device which is prone to failure when, or if, the adhesive holding the bandage fails. The application method with the need to press the pad against the patient also makes accurate location of the bandage difficult.

The present invention provides a wound dressing applicator as defined in independent claims 1, 26, 32 and 33 to which reference should now be made.

Some preferred features of the invention are set out in dependent claims 2 to 25 and 27 to 31 to which reference should now be made.

The inventors of the present invention have taken the counter-intuitive step of providing a rigid wound dressing applicator that is more complicated to make than the known types of wound dressing application systems. This is to provide a simple, effective and robust applicator for wound dressings and one which overcomes the problems associated with the known flexible wound dressing application systems.

An advantage of the wound dressing applicator of the invention being rigid is that, unlike the known dressing applicator systems, the wound dressing is effectively protected during transit and handling of the applicator. Furthermore, the applicator can be handled in a controlled manner such that the wound dressing can easily and accurately be positioned over a wound.

The rigid enclosure provided in the rigid body means that soft, gel-like, moist wound dressings such as hydrocolloid dressings can be applied to a patient's skin using the applicator, in addition to the simple adhesive bandages that are commonly used with the known systems. When these gel-like materials are used, they are protected and located by the rigid enclosure.

A further advantage of the wound dressing applicator of the invention is that, unlike the known systems, the applicator is not made up of a series of layers joined by adhesives of varying properties. This means that the applicator of the invention is not reliant on the correct adhesion between the various components for it to work as designed. The present applicator provides a simple and easy-to-operate, mechanical solution to the need for a reliable applicator for applying wound dressings. Furthermore, this eliminates the risk associated with the known systems that the protective layers for the wound dressing may peel apart prematurely, thereby contaminating the dressing, or that the wound dressing may be separated prematurely from its support pieces or handle portions, rendering it unusable.

Another advantage of the applicator of the invention is that the rigid applicator body with rigid enclosure enables the user to apply the dressing to a wound in a controlled manner using only one hand. This reduces the need to handle the applicator, thereby reducing the chances of the dressing being contaminated, and leaves one of the user's hands free to provide stability when leaning over to reach a wound or to perform other tasks.

The ejector enables the user to apply a force to the wound dressing to urge it out of the rigid body recess and into contact with the patient's skin, whilst handling the dressing aseptically. When a moist wound dressing is held in the rigid body enclosure, the ejector can also be used to overcome any surface tension and/or vacuum forces which arise at the interface between the moist dressing and the body enclosure.

Preferably, the ejector is a biased lever. This means that when a force applied to the ejector to urge the wound dressing out of the body enclosure is removed, the ejector returns to its original or rest position under its own bias.

Preferably, a rigid cover is provided to cover the rigid enclosure. This protects a wound dressing placed in the rigid enclosure during transport and handling of an applicator and lid assembly. Preferably the rigid lid has a lid ejector. The combination of a rigid lid and a lid ejector enables the lid to be used as an applicator in the event that the wound dressing is adhered to the lid when the lid is removed from the applicator to expose the wound dressing.

Preferably, the wound dressing applicator has a handle portion at a distal end of the applicator, while the body enclosure is at a proximal end of the applicator. This facilitates gripping of the applicator at a location that is spaced apart from the enclosure containing the wound dressing. This allows controlled, precise and comfortable movement of the wound dressing to the wound area, whilst handling the wound dressing aseptically. The handle also adds to the applicator's aesthetic qualities.

A preferred embodiment of the present invention will be described, by way of example only, with reference to the attached figures. The figures are only for the purposes of explaining and illustrating a preferred embodiment of the invention and are not to be construed as limiting the claims. The skilled man will readily and easily envisage alternative embodiments of the invention in its various aspects.

Figure 1:
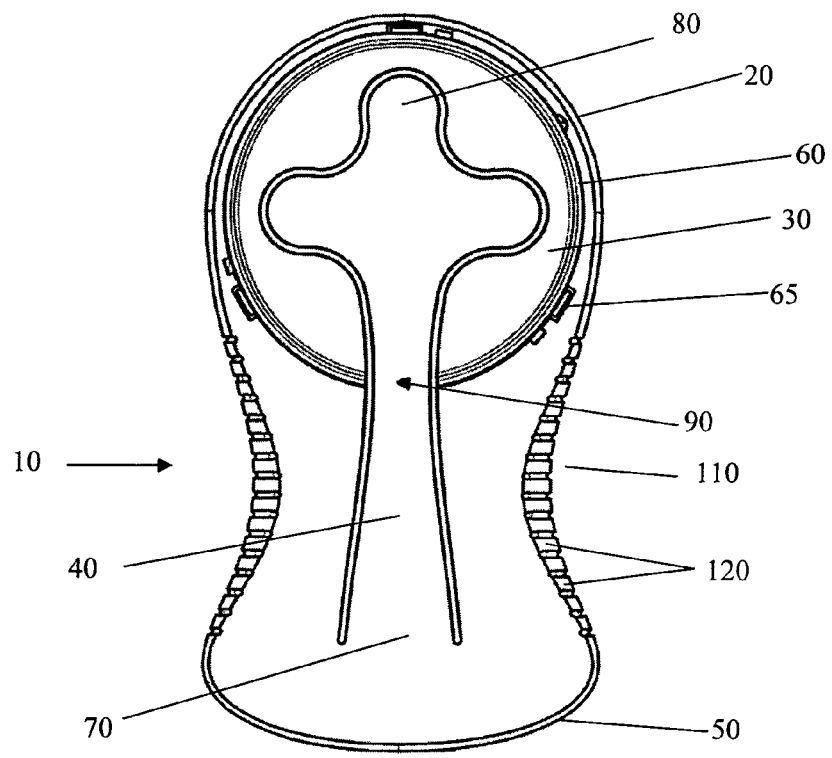
FIG. 1 is a view of a front surface of a wound dressing applicator embodying the invention.
Figure 2:
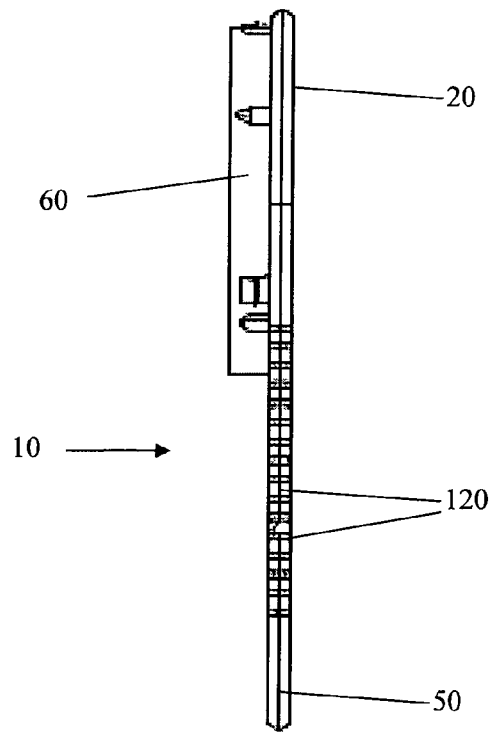
FIG. 2 is a side view of the wound dressing applicator of FIG. 1.

A wound dressing applicator (10) (see FIGS. 1 and 2) comprises a rigid body (20) having a rigid enclosure (30) for receiving a wound dressing. The applicator further comprises a push-out element or ejector (40) for ejecting or pushing out the wound dressing from the enclosure, and a handle (50) for gripping the applicator. The rigid body enclosure (30) and handle (50) are located at a proximal end and a distal end of the applicator respectively.

The body enclosure (30) is defined by a wall (60) extending perpendicularly from the rigid body (20). This provides an enclosure in the form of an open-top cylinder, the bottom of the cylinder being a surface of the rigid body, which provides a flat planar base to the rigid enclosure (30).

The shape of the enclosure depends on the shape of the wound dressing. In alternative embodiments of the invention, the enclosure could be other shapes. Furthermore, the enclosure could also be a recess in the rigid body itself.

A wound dressing (not shown) can be placed into the body enclosure (30) using, for example, a pair of forceps or other suitable handling apparatus. Preferably the wound dressing compound is a thin disc of soft, gel-like material, such as "ICX-PRO" gel as described in PCT patent application no. PCT/GB2005/000523. Such compositions contain living cells. In preferred embodiments of the invention, the wound dressing is a composition containing living human cells, preferably fibroblasts, more preferably human dermal fibroblasts. The wound dressing can be kept in a moist state during storage and transportation, by the addition of a suitable medium.

The body ejector (40) is moveable relative to the rigid body (20) and into the body enclosure (30) to push against the wound dressing to urge it out of the rigid body enclosure (30).

The body ejector (40) is preferably formed during manufacture of the applicator. The ejector is a biased lever, or cantilever beam, having a first end (70) attached to the rigid body and second end (80) spaced from the first end (70) and moveable relative to the rigid body (20).

When a force is applied to the second or free end (80) of the body ejector (40), in a direction that is substantially perpendicular to the rigid body, the biased body ejector flexes about its first end (70) attached to the rigid body. When the force is removed, the biased ejector springs back to the position it occupied in the absence of an applied force. Preferably, at rest (i.e. when not under the application of a force) the ejector lies flush with the rigid body (20).

The wall of the rigid enclosure (30) has a slot (90) to allow the free end (80) of the body ejector to move, under the application of a force, from its rest position to a position where the wound dressing is pushed out of the enclosure (30).

Figure 3:
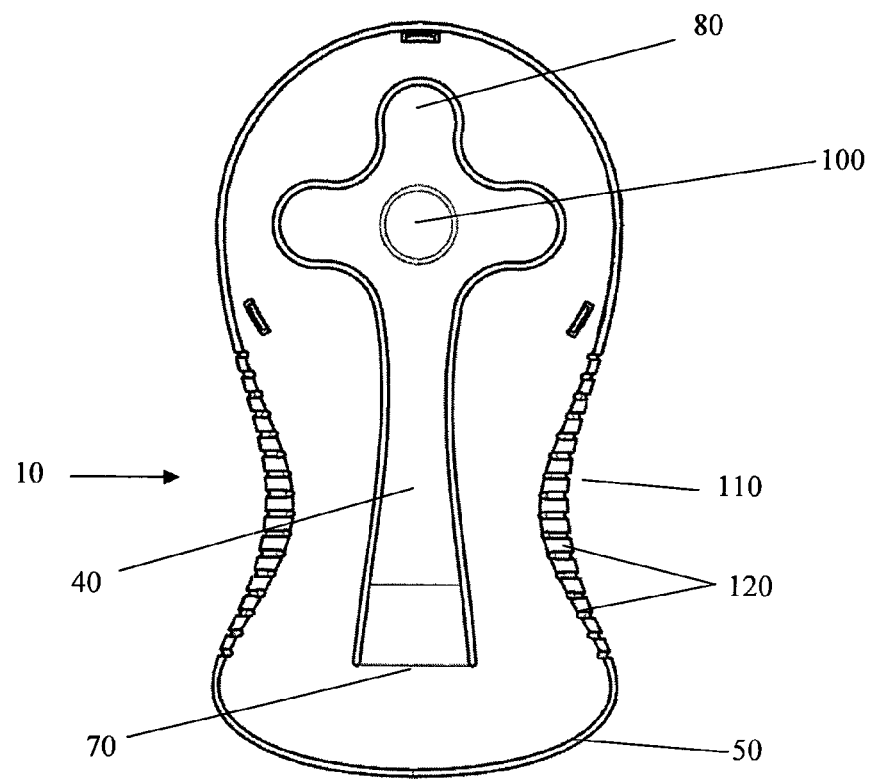
FIG. 3 is a view of a rear surface of the wound dressing applicator of FIGS. 1 and 2.

The body ejector may have a dimple (100) (see FIG. 3) or other suitable feature in which the user's finger can easily be located so that the body ejector can be used to eject the wound dressing from the rigid enclosure (30) in a controlled motion.

The handle portion (50) of the rigid body (20) has indentations (110) having gripping elements (120), enabling the user to grip the wound dressing applicator (10) firmly and comfortably.

In the preferred embodiment (shown in FIGS. 1 to 3), the rigid enclosure is covered by a rigid lid (200) as shown in FIG.

4. The lid may be simple cover having a sealing fit with the rigid body, or may have retaining clips (not shown) or be threaded (not shown) to secure the lid to the applicator.

Figure 4:
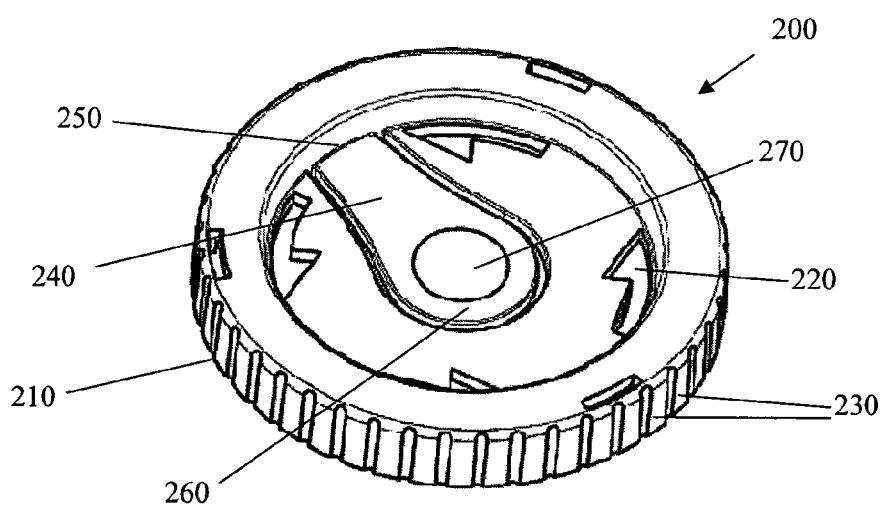
FIG. 4 is a perspective view of a rigid lid for the applicator of FIGS. 1 to 3.

The lid (200) (see FIG. 4) may be dimensioned to fit inside the wall (60) that defines the rigid body enclosure (30) and engage with an inside surface of the wall. Alternatively, the lid may be dimensioned to cover the wall (60) of the enclosure (30), by engaging with an outside surface of the wall.

The lid comprises retaining clips (not shown) on an inside surface of an outer rim (210) of the lid which engage with complementary retaining clips (65—see FIG. 1) on an outside surface of the wall (60) that defines the enclosure (30). This allows the lid to be clipped onto the rigid body (20) to cover the rigid enclosure and enclosure wall. Rotation of the lid relative to the rigid body, for example, in the direction indicated by arrows (220), disengages the complementary retaining clips so that the lid can be removed from the applicator, thereby exposing the wound dressing. Ridges (230) may be provided on the outer rim (210) of the lid (200) to allow the user to grip the lid firmly in order to rotate it relative to the applicator.

The lid has one or more open regions which may be in the form of arrows (220). In addition to indicating the direction of rotation of the lid, the open regions allow the wound dressing to be bathed in a suitable medium during storage and transportation of a wound dressing applicator and lid assembly which contains the wound dressing. Furthermore, the open regions allow air to pass through the lid and into the rigid lid enclosure, to circulate between an inside surface of the lid and the moist wound dressing. This is designed to prevent the surface tension and vacuum forces at the moist dressing/lid interface, from adhering the moist wound dressing to the lid when the lid is removed from the applicator to expose the dressing. The open regions are sufficiently large to allow air to pass through the lid but sufficiently small to prevent the wound dressing, when in gel-form, from escaping through the open regions.

The lid has an ejector (240) and a lid enclosure (not shown) at an inside surface of the lid, the enclosure having a flat planar base. The lid ejector (240), as with the body ejector (40), is a biased lever fixed at a first end (250) to the lid and moveable relative to the lid at a second end (or free end) (260). The free end of the lid ejector (260) is moveable into the lid enclosure to urge the wound dressing out of the lid enclosure.

The lid ejector (240) may have a dimple (270) (see FIG. 4) or other suitable feature in which the user's finger can easily be located so that the body ejector can be used to eject the wound dressing from the lid enclosure (not shown) in a controlled motion.

The provision of a lid ejector (240) means that in the event that the applicator and lid assembly is inverted, say during transportation, and the wound compound remains in the lid enclosure and adhered to the lid when it is removed from the applicator, the lid (200) can itself operate as a wound dressing applicator, as the lid ejector can be operated to eject the wound dressing from the lid enclosure.

The applicator comprising the ejector, enclosure and handle and the lid comprising the lid enclosure and lid ejector are made from suitable medical grade materials such as inert polymers, for example, USP class VI virgin grade transparent PET (polyethylene terephthalate). The transparency of the applicator and lid ensures that the user can see the position of the wound dressing through the applicator and lid assembly and can therefore accurately locate the wound dressing over a patient's wound when handling the wound dressing using the applicator or lid.

In an alternative embodiment, a flexible cover (not shown) such as a peelable PET layer, may be provided to cover the rigid enclosure (30). This could be used to protect the wound dressing during transportation and handling of the wound dressing applicator and/or to retain the wound dressing in the rigid enclosure.

In use, the wound dressing applicator is gripped by the user in one hand at indentations (110) of the handle (50) and positioned so that the lid is on a top surface of the applicator. The lid (200) is gripped in the user's remaining hand and rotated so that the retaining clips (not shown) on the lid (200) are disengaged from those (65—see FIG. 1) on the applicator, allowing the lid to be removed from the applicator.

If, when the lid is removed from the applicator, the wound dressing remains located in the rigid body enclosure (30), the lid is discarded. The applicator with exposed wound dressing is moved near to the location of the patient's wound and inverted so that the exposed surface of the wound dressing faces the patient's skin. When a moist wound dressing is used, vacuum and/or surface tension forces at the interface between the moist dressing and the rigid body enclosure could retain the moist wound dressing in the body enclosure when the applicator is inverted.

The body ejector (40) is operated by the user applying a manual force, preferably with a finger, for example the index finger of the hand in which the applicator rigid body is gripped, to the free end (80) of the body ejector. When sufficient force is applied to the ejector to overcome the bias and any surface tension and/or vacuum forces which adhere the moist wound dressing to the applicator, the ejector is pushed through the body enclosure, ejecting the wound dressing from the enclosure to cover the wound. The wound dressing then remains on the wound, whereupon the applicator is removed and discarded.

If, however, when the lid is removed from the applicator, the moist wound dressing is adhered to the lid, the applicator is discarded and the lid (200) itself is used as a wound dressing applicator. The lid with exposed wound dressing is moved near to the location of the patient's wound and inverted so that the exposed surface of the wound dressing faces the patient's skin. When a moist wound dressing is used, vacuum and/or surface tension forces at the interface between the moist dressing and the rigid lid enclosure could retain the moist wound dressing in the lid enclosure when the lid is inverted.

The lid ejector (240) is operated by the user applying a manual force, preferably with a finger, for example the index finger of the hand in which the applicator lid is gripped, to the free end of the lid ejector. When sufficient force is applied to the lid ejector to overcome the bias and any surface tension and/or vacuum forces arising at the interface between the moist dressing and the rigid lid, the lid ejector is pushed through the lid enclosure, ejecting the wound dressing from the lid enclosure to cover the patient's wound. The wound dressing then remains on the wound whereupon the lid is removed and discarded.

Alternatively, a projection or other feature may be provided on the lid to allow it to be gripped and removed from the applicator using, for example, a pair of forceps. This ensures that the lid does not have to be handled by the user, which is particularly important where aseptic handling of the lid is required.

Figure 5:
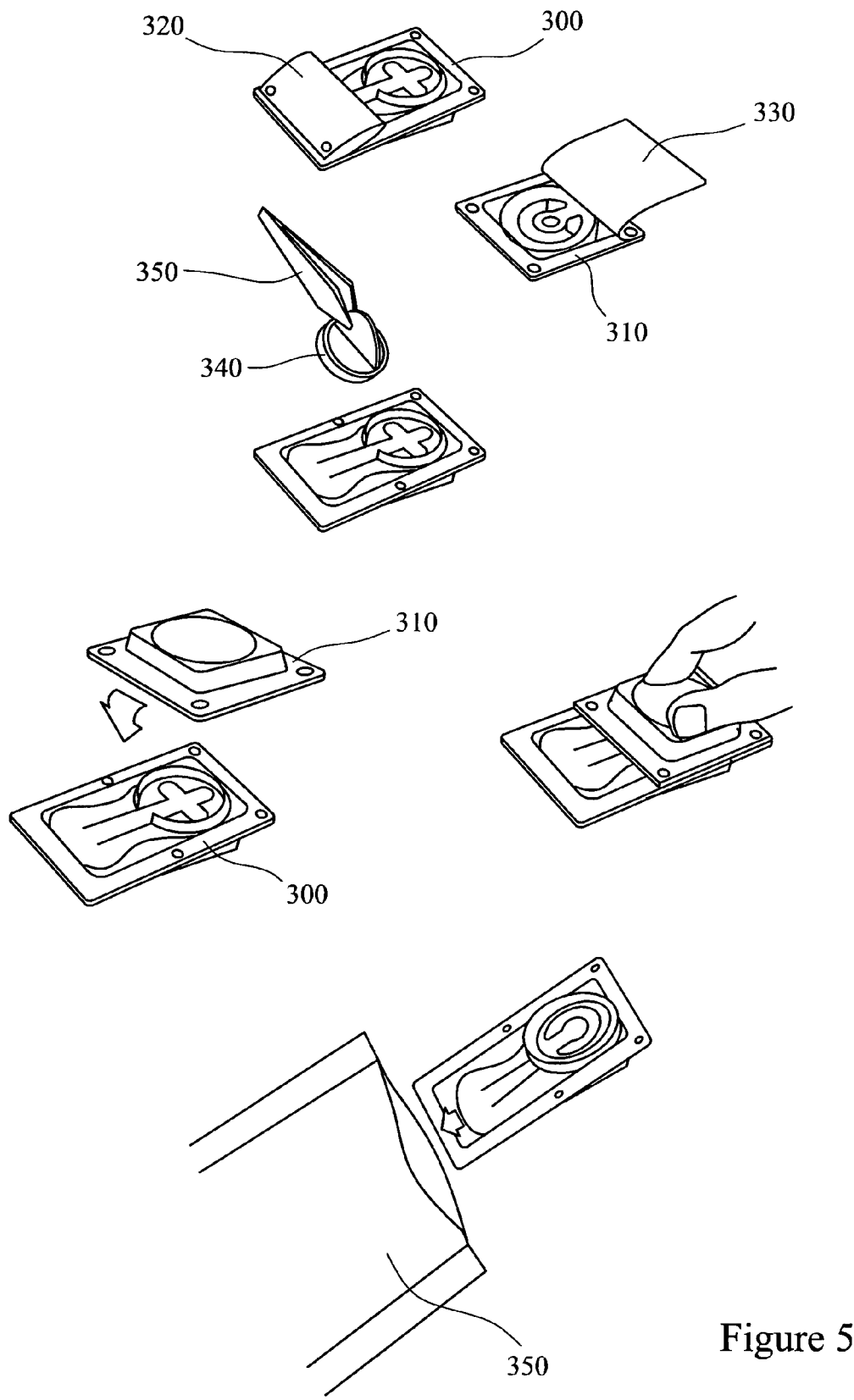
FIG. 5 is a diagram illustrating a method of assembling the applicator of FIGS. 1 to 3 and the lid of FIG. 4 without the need for handling the components themselves.

The invention also provides a method of assembling the applicator and lid of the preferred embodiment of the invention so that neither of the components must be handled prior to the applicator being used to apply a wound dressing to a patient's skin (see FIG. 5). This is particularly important where aseptic handling of wound dressings and assembly of wound dressing applicator and lid assemblies is required.

Figure 6:
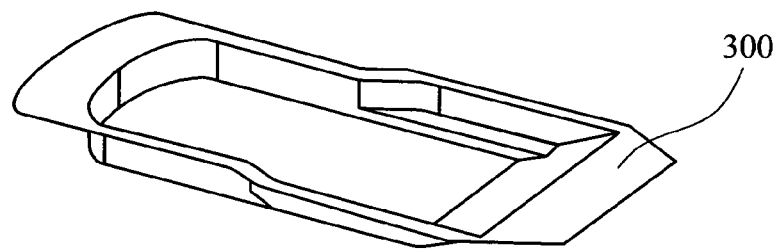
FIG. 6 is a close up view of the applicator packaging of FIG. 5.
Figure 7:
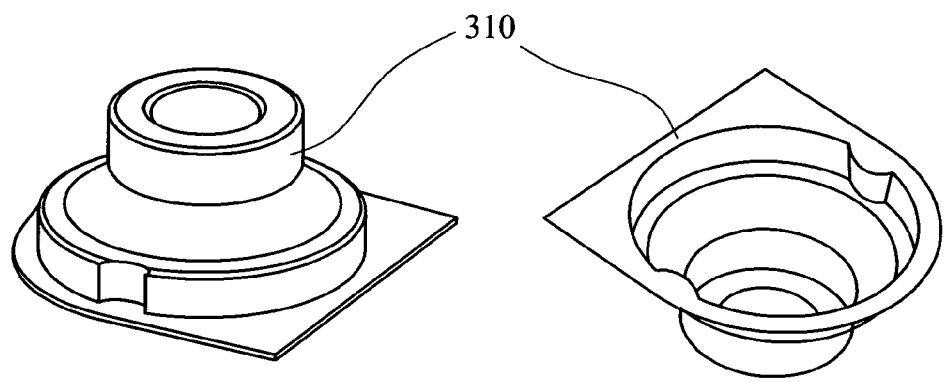
FIG. 7 is a close up view of the lid packaging of FIG. 5.

The applicator (10) and lid (200) components are each packaged separately following their original manufacture and each of the applicator and lid packaging (300, 310) is sealed using, for example, a peelable sheet of material such as a peelable PET layer (320, 330). A close up of each of the applicator and lid packaging is shown in FIGS. 6 and 7 respectively. When assembly is required, the peelable cover is removed from each of the applicator and lid packaging to expose the rigid body enclosure of the applicator and the rigid lid enclosure of the rigid lid.

A wound dressing such as a disc of ICX-PRO gel (340), is transported from a container such as a Petri dish using, for example, a pair of forceps (350) or the like, and laid into the rigid enclosure of the applicator while it remains in its packaging (300).

The lid (200) has a sealing fit in the lid packaging (310) and the lid packaging (310) is shaped to allow an operator to grip the packaging without handling the lid (200) itself. The operator can therefore transport the lid by handling the lid packaging, preferably by gripping the packaging with the thumb and forefinger of one hand. The lid packaging is used to locate the lid adjacent to the applicator and to press the lid onto the applicator until the complementary retaining clips on the lid engage with those on the enclosure wall of the applicator. The lid packaging (310) is then removed from the assembled lid and applicator and discarded.

The assembly is then inserted into, for example, a foil pouch (350) by using the retainer packaging (300) to guide the assembly into the pouch so that the applicator and lid components themselves need not be handled. The pouch (350) is sealed and the original applicator packaging (300) is discarded. The applicator and lid assembly can then be transported in the sealed pouch, ensuring that the applicator remains sterile, until the user that opens the pouch uses the applicator assembly to administer the wound dressing to a patient. The pouch may contain a suitable medium to keep the wound dressing moist during storage and transportation of the pouch.

Figure 8:
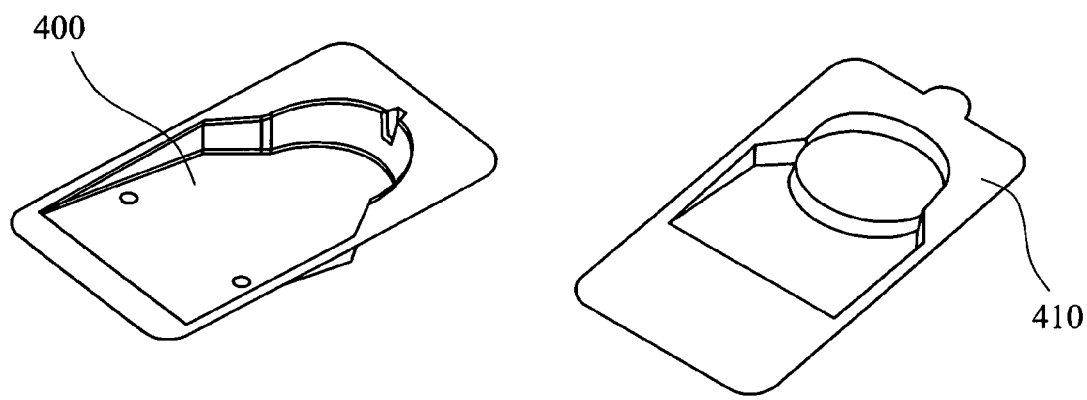
FIG. 8 is a close up view of the applicator and lid assembly packaging of FIG. 5.

Alternatively, the applicator and lid assembly may be repackaged in a thermoformed container (400) with a peelable cover (410), the packaging being shaped according to the profile of the applicator and lid assembly (see FIG. 8). This container may also include a suitable medium for bathing the wound dressing to keep it moist and could tightly enclose the assembled applicator and lid to provide support to the assembly during storage and transportation and to reduce the quantity of medium required to bathe the wound dressing to keep it moist.

The invention claimed is:

1. A wound dressing applicator comprising:
  a rigid body having a rigid body enclosure for a wound dressing, wherein the rigid body enclosure is defined by a wall extending from the rigid body;
  an ejector for ejection of a wound dressing from the rigid body enclosure, wherein the ejector is a biased lever that is coupled to the rigid body enclosure, and wherein the ejector is moveable relative to the rigid body enclosure to push a wound dressing out of the rigid body enclosure; and
  a removable rigid lid over the rigid body enclosure, wherein the rigid lid comprises an ejector for ejection of a wound dressing from the rigid lid.

2. A wound dressing applicator according to claim 1 wherein the cover is flexible.

3. A wound dressing applicator according to claim 1 wherein the lid comprises a rigid lid enclosure.

4. A wound dressing applicator according to claim 1 wherein the wall extends perpendicularly from the rigid body.

5. A wound dressing applicator according to claim 1 wherein the lid is coupleable to the wall.

6. A wound dressing applicator according to claim 5 wherein the lid fits inside the enclosure wall.

7. A wound dressing applicator according to claim 5 wherein the lid fits over the enclosure wall.

8. A wound dressing applicator according to claim 1 wherein the applicator includes a handle.

9. A wound dressing applicator according to claim 8 wherein the rigid enclosure is at a proximal end of the applicator and the handle is at distal end of the applicator.

10. A wound dressing applicator according to claim 1 wherein the lid has one or more open regions.

11. A wound dressing applicator according to claim 1 made of transparent material.

12. A wound dressing applicator according to claim 1 wherein the lid is made of transparent material.

13. A wound dressing applicator according to claim 1 wherein the rigid enclosure holds a moist wound dressing and, in use, the ejector coupled to the rigid body enclosure breaks a seal between the moist dressing and the applicator.

14. A wound dressing applicator according to claim 1 wherein the rigid enclosure holds a hydrocolloid wound dressing.

15. A wound dressing applicator according to claim 1 wherein the rigid enclosure holds a wound dressing containing living cells.

16. A wound dressing applicator according to claim 15 wherein the human cells are dermal fibroblasts.

17. A kit for applying a wound dressing comprising: a wound dressing applicator according to claim 1; a wound dressing for placement into the rigid enclosure; and a rigid cover for covering the rigid enclosure.

18. A kit for applying a wound dressing according to claim 17 wherein the wound dressing is a hydrocolloid dressing or wherein the wound dressing comprises living human dermal fibroblasts.

* * * * *

UNITED STATES PATENT AND TRADEMARK OFFICE
CERTIFICATE OF CORRECTION

PATENT NO. : 8,722,962 B2  Page 1 of 1
APPLICATION NO. : 12/809518
DATED : May 13, 2014
INVENTOR(S) : Dera et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 795 days.

Signed and Sealed this

Twenty-ninth Day of September, 2015

Michelle K. Lee
*Director of the United States Patent and Trademark Office*